Figure 1:
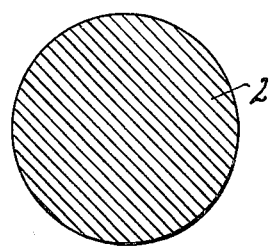

United States Patent [19]
Koch

[11] 4,203,432
[45] May 20, 1980

[54] MALE THERAPEUTIC DEVICE

[76] Inventor: Edward G. Koch, 716 Benton Blvd., Kansas City, Mo. 64124

[21] Appl. No.: 965,831

[22] Filed: Dec. 4, 1978

[51] Int. Cl.$^2$ ............................................... A61F 5/00
[52] U.S. Cl. ..................................................... 128/79
[58] Field of Search ................ 128/79, 327, DIG. 25, 128/138, 87 R

[56] References Cited
U.S. PATENT DOCUMENTS

| | | | |
|---|---|---|---|
| 3,612,047 | 10/1971 | Nesbit | 128/79 |
| 3,636,948 | 1/1972 | Atchley | 128/78 |
| 3,759,253 | 9/1973 | Cray | 128/79 |
| 3,794,020 | 2/1974 | Bagby | 128/79 |
| 4,139,007 | 2/1979 | Diamond | 128/138 R |

*Primary Examiner*—Lawrence W. Trapp
*Attorney, Agent, or Firm*—John A. Hamilton

[57] ABSTRACT

A device for assisting males in producing and maintaining erection of the penis, consisting of a split ring of flexible but substantially inextensible material adapted to be engaged about the organ with its ends spaced apart peripherally of the organ, the ring having internal lugs formed thereon so as to engage the organ around only a portion of the circumference and to be spaced apart therefrom around the remainder of the circumference, and an elastic band connecting the ends of the ring to secure the latter in place, the band being adjustable to vary both the diameter of the ring to the diameter of the organ, and the pressure with which the ring grips the organ.

5 Claims, 5 Drawing Figures

U.S. Patent

May 20, 1980

4,203,432

MALE THERAPEUTIC DEVICE

This invention relates to new and useful improvements in therapeutic devices for assisting males who have problems in this respect to produce and maintain erections of the penis.

An erection is produced when arterial blood flows to the erectile tissues of the penis, but the veinal return flow of blood to the body is restricted, so that the erectile tissues become engorged with blood. The restriction is normally performed by certain sphincter muscles, functioning in response to sexual arousal, but particularly in men of advancing age, or men having certain physiological or psychological malfunctions, these sphincter muscles apparently do not function properly, or relax prematurely before coitus can be completed, rendering the sex act quite unsatisfactory. It is to a solution of this problem that the present invention is directed.

By taking advantage of the known fact that the penile arteries are disposed principally in the deep interior of the organ, and the return veins are disposed principally sub-dermally adjacent its surface, it has long been known that the return veinal blood flow can be restricted by securing a band, in the nature of a tourniquet, around the base of the organ closely adjacent the body. This assists in the maintenance of erection by restricting the return veinal blood flow, while the arterial flow remains substantially unimpeded since the arteries are deeply embedded and protected from pressure by the erectile tissues. However, this type of device, as well as certain other types of spring clip or clamping devices which have also been previously proposed, is subject to certain disadvantages. It is difficult or impossible to adjust to provide the proper degree of veinal restriction. Too little restriction will prevent it from performing its intended function of maintaining an erection, and too great a degree of restriction will result in discomfort, numbness, insensitivity, and even damage to the flesh if left applied for too long a time. Also, the degree of restriction for a given "setting" will depend on the degree of erection, so that such a device originally set to a tightness suitable for an initial erection may become too tight as the sex act proceeds and the user approaches actual orgasm. Additionally, difficulties are usually experienced in providing a proper setting for comfort and desired pressure when the penis itself is of different sizes. The diameter and circumference of the penis varies considerably from one person to another.

Accordingly, one object of the present invention is the provision of a device of the character described which, while basically consisting of a constricting ring adapted to be applied about the penis, is nevertheless so constituted and configurated that it cannot compress the entire circumference of the organ no matter how tightly it may be applied, and thus cannot restrict the return veinal blood flow to the extent of causing numbness or insensitivity. For this purpose, the ring is formed of a semi-hard though flexible material, and is provided around its interior periphery with inwardly projecting lugs for contacting only a portion of the periphery of the penis, while holding the remaining portions of the ring in spaced apart relation from the penis.

Another object is the provision of a device of the character described having novel and extremely simple means for adjusting the ring to male organs of different diameters, and for adjusting the constricting pressure of the ring. It also provides an extremely rapid means for disengaging and removing the ring from the organ whenever desired.

Other objects are simplicity and economy of construction, comfort and convenience of use, and efficiency and dependability of operation.

Figure 2:
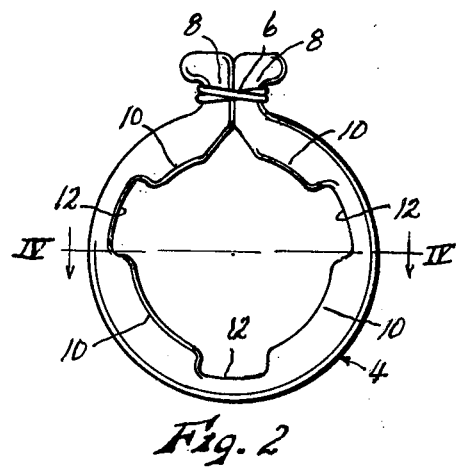
Figure 3:
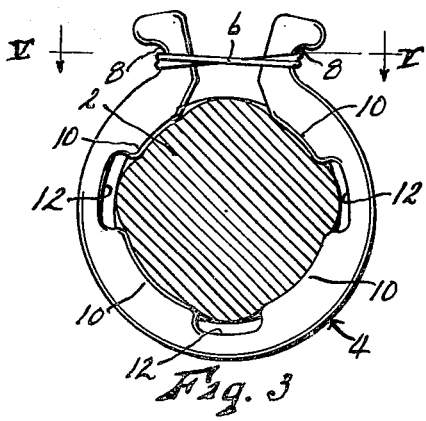
Figure 4:
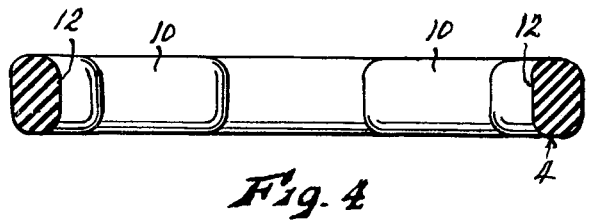
Figure 5:
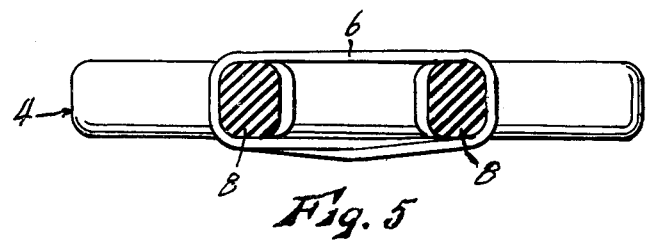

With these objects in view, as well as other objects which will appear in the course of the specification, reference will be had to the accompanying drawing, wherein:

FIG. 1 is a diagrammatic cross sectional view of a male penis, in a state of erection, FIG. 2 is a face view of a therapeutic device embodying the present invention, FIG. 3 is a view similar to FIG. 1, showing the therapeutic device operatively applied to the penis, FIG. 4 is an enlarged sectional view taken on line IV—IV of FIG. 2, and FIG. 5 is an enlarged sectional view taken on line V—V of FIG. 4, with the penis omitted.

Like reference numerals apply to similar parts throughout the several views, and in FIGS. 1 and 3, the numeral 2 applies to a diagrammatic cross sectional view of a male penis in a state of erection. The penis is of course not precisely circular in cross section, but the showing will serve adequately to illustrate the function of the present therapeutic device.

The device constituting the subject matter of the present invention includes a ring designated generally by the numeral 4, and an elastic connector 6 which may constitute an endless rubber band. Ring 4 is split to form a single continuous length the major portion of which is formed in circular shape, as shown in FIGS. 2 and 3, with the extreme end portions thereof formed to extend radially outwardly, at the split of the ring, and then tangentially and outwardly in opposite directions, in outwardly spaced relation from the body of the ring but lying in the plane thereof, whereby to form outwardly and oppositely opening hook configurations 8. The outer periphery of the body of the ring is normally circular, but its inner periphery has a series of angularly spaced apart, radially inwardly projecting lugs 10 formed integrally therewith, with notches 12 alternating with said lugs. The inner surfaces of lugs 10 also normally define a circle, as shown in FIG. 2. The aggregate angular extent of all of lugs 10 (4 as shown) is subject to variation as will be more fully discussed hereinbelow. The cross sectional shape of the strand forming the ring is preferably generally rectangular, as shown in FIG. 4, but all corners and edges are rounded to prevent cutting or pinching of the flesh thereby. The material of which the ring is formed is of considerable importance, at least as to the characteristics thereof though any suitable specific material may be used. The material should be such that in any substantial length of the strand forming the ring, said strand is freely flexible to a substantial degree, but nevertheless still sufficiently firm that it resists abrupt local deformation, is not locally compressible to any large degree, and such that the strand forming the ring is not longitudinally elastically extensible to any appreciable degree, at least within the tensions likely to be applied thereto in the present usage. A semi-hard rubber, or soft plastic, such as certain polyethylene resins, meet these requirements. Connector 6 consists of an endless band of highly stretchable material, such for example as latex rubber, looped one or more times (two loops being shown)

around the hook elements 8 of the ring to join the ends of said split ring yieldably together.

In use, connector band 6 is removed, and the ring deformed to fit it about the base of penis 2 closely adjacent the body. If properly sized for the user, the ends thereof carrying hooks 8 will then be spaced angularly apart, as shown in FIG. 3. Connector band 6 is then again looped into hook portions 8 of the ring as shown, thereby contracting the ring firmly about the penis, with lugs 10 in indenting relation to the organ so as to restrict return flow of blood to the body in a portion of the veins of the organ close to its surface to assist in the maintenance of erection as previously described, while the ring portions within notches 12 do not engage the organ at all, or only lightly, so as not to interfere with veinal circulation in those portions of the periphery of the organ. By restricting the veinal flow in only a portion of the periphery, the numbness and insensitivity which would result from a more complete constriction is avoided. Band 6 may be removed very rapidly and easily to disengage the ring in the event of any sudden pain or discomfort.

The flexibility of the ring permits it to accomodate itself readily to the commonly somewhat non-circular cross sectional contour of the penis. Its rectangular cross sectional shape causes it to present a generally cylindrical surface, defined by lugs 10, to the penis, so as to resist any tendency of the ring strand to roll, or twist around the axis of its peripheral extent. Its general inextensibility, longitudinally of the strand forming it, allows the pressure exerted thereby on the penis to be regulated virtually solely by rubber band 6. Said rubber band may be looped around hooks 8 from one to several times, and the more loops that are used, the greater the constricting pressure the ring applies to the penis. Normally the ring should be worn as tightly as the user may comfortably endure for the required period of time, and the rubber band provides a ready means for adjusting said tightness as may be desired. While the hook ends of the ring must be spaced apart when applied to the penis, in order to allow the rubber band to take effect, they may be spaced apart to a greater or lesser degree depending on the erect diameter of the penis. With a penis of greater diameter, hooks 8 will be more widely spaced apart, and fewer loops of band 6 will be required to apply the same constrictive pressure to the penis. Conversely, with a penis of smaller diameter the hooks will be more closely spaced, and more loops of band 6 will be required. Thus band 6 provides the dual function of both adjusting the ring to organs of different diameters, and also of adjusting the constrictive pressure applied thereby. The band is also readily yieldable to avoid undue constricture of the organ in the event it should expand to a fuller degree of erection at certain stages of the sex act. A single ring should be applicable to all male organs over a normal range of average diameters, being accomodated thereto simply by a variation in the spacing between hooks 8. Organs either smaller or larger than average to too great a degree will require rings of smaller or larger normal diameters.

As shown, the aggregate angular extent of lugs 10 is about 50% of the ring circumference. This has been found in use to provide sufficient reduction of veinal blood flow to maintain erection in most cases. However, this proportion could be increased or decreased for individual users, depending on their requirements for greater or lesser constriction. In any case, said lugs should be distributed about the periphery of the ring so as to support said ring generally concentrically to the organ, and it is generally advisable to provide a notch 12 at the lower or ventral side of the penis, since a lug 10 at that point would constrict the urethra, and hence interfere with seminal ejaculation.

While I have shown and described a specific embodiment of my invention, it will be readily apparent that many minor changes of structure and operation could be made without departing from the spirit of the invention.

What I claim as new and desire to protect by Letters Patent is:

1. A therapeutic device for assisting in the maintenance of erection in the male penis, and comprising:
 a. a ring of flexible but relatively inelastic material adapted to encircle the base of the penis closely adjacent the body, and having angularly spaced apart, radially inwardly projecting lugs at the inner periphery thereof, said lugs alternating with recessed notches, one of said notches being disposable at the ventral side of the penis whereby to avoid constriction of the urethra, and
 b. constricting means operable to contract said ring resiliently about the penis to press said lugs firmly against the penis, whereby said lugs constrict and reduce veinal flow of blood in the portions of the penis periphery engaged thereby, but not in the portions of said periphery not engaged thereby.

2. A device as recited in claim 1 wherein the cross sectional form of said ring is generally rectangular, whereby said lugs present a generally cylindrical form, defined in skeleton form by the inner peripheries of said lugs and concentric with said ring, to the penis, whereby to resist rolling or twisting of said ring.

3. A device as recited in claim 1 wherein said ring is split to form a circular strand having two ends, and is of such circumference that when it is positioned about the penis, its ends are angularly spaced apart, and wherein said constricting means comprises an elastic tensile member extending between and interconnecting the ends of said ring strand, whereby to contract said ring strand about the penis.

4. A device as recited in claim 3 wherein said elastic tensile member is adjustable in tension, whereby to adjust the contraction force exerted on the penis by said ring, and whereby to adjust the ring to penises of different diameters.

5. A device as recited in claim 3 wherein each end of said ring strand is configured to form a re-entrant hook disposed outside of the general diameter of said ring, and wherein said elastic tensile member comprises an endless elastic band looped around said hooks to bias said ring strand ends toward each other, the tensile force exerted by said band being variable by the number of times it is looped about said hooks.

* * * * *